(12) United States Patent
Park et al.

(10) Patent No.: US 7,255,717 B2
(45) Date of Patent: Aug. 14, 2007

(54) FEMORAL HEAD SURFACE REPLACEMENT SYSTEM

(76) Inventors: Myung-sik Park, 2-910 Keoseong-Green Apartment, Junghwasan-dong, Wansan-gu, Jeonju-si, Jeonbuk (KR); Hyung-bae Park, 2-910 Keoseong-Green Apartment, Junghwasan-dong, Wansan-gu, Jeonju-si, Jeonbuk (KR)

(*) Notice: Subject to any disclaimer, the term of this patent is extended or adjusted under 35 U.S.C. 154(b) by 0 days.

(21) Appl. No.: 10/934,756

(22) Filed: Sep. 3, 2004

(65) Prior Publication Data

US 2005/0256585 A1  Nov. 17, 2005

(30) Foreign Application Priority Data

May 13, 2004 (KR) ...................... 10-2004-0033891

(51) Int. Cl.
*A61F 2/36* (2006.01)
(52) U.S. Cl. ................................. 623/23.12; 623/23.14
(58) Field of Classification Search ............ 623/23.14, 623/23.12, 23.13, 19.13, 19.14
See application file for complete search history.

(56) References Cited

U.S. PATENT DOCUMENTS

| | | | | |
|---|---|---|---|---|
| 3,053,251 A | * | 9/1962 | Black et al. ............. | 623/23.12 |
| 3,979,778 A | * | 9/1976 | Stroot ...................... | 623/19.12 |
| 4,752,296 A | * | 6/1988 | Buechel et al. .......... | 623/23.14 |
| 5,133,764 A | * | 7/1992 | Pappas et al. ........... | 623/23.14 |
| 5,658,340 A | * | 8/1997 | Muller et al. ............ | 623/19.14 |
| 5,800,557 A | * | 9/1998 | Elhami ..................... | 623/23.12 |
| 5,868,796 A | * | 2/1999 | Buechel et al. .......... | 623/16.11 |
| 6,096,084 A | * | 8/2000 | Townley .................. | 623/23.12 |
| 6,508,841 B2 | * | 1/2003 | Martin et al. ............ | 623/23.12 |
| 2003/0014123 A1 | * | 1/2003 | Copf et al. .............. | 623/23.14 |
| 2004/0024468 A1 | * | 2/2004 | Lualdi et al. ............ | 623/22.45 |

FOREIGN PATENT DOCUMENTS

FR   2578739   *   9/1986

* cited by examiner

*Primary Examiner*—Alvin J. Stewart
(74) *Attorney, Agent, or Firm*—Greenlee, Winner and Sullivan, P.C.

(57) ABSTRACT

Provided is a femoral head surface replacement system including a femoral head aspherical cup having a round cavity inside and a distal end having an open lower end, and a stem installed on the femoral head aspherical cup and extending to a lower side end thereof. In the femoral head aspherical cup, a cavity is formed so that a femoral head is inserted therein, a conic insertion protrusion protrudes from an upper side of the cavity, and the distal end is formed of a plurality of protruding portions and groove portions. In the stem, an insertion hole is formed corresponding to the insertion protrusion of the femoral head aspherical cup so that the stem is fixed to the femoral head aspherical cup as the insertion protrusion is forcibly inserted into the insertion hole.

7 Claims, 3 Drawing Sheets

FEMORAL HEAD SURFACE REPLACEMENT SYSTEM

CROSS REFERENCE TO RELATED APPLICATIONS

This application claims benefit of Korean Patent Application No. 10-2004-0033891, filed May 13, 2004, which is incorporated herein by reference to the extent not inconsistent herewith.

BACKGROUND OF THE INVENTION

1. Field of the Invention

The present invention relates to a femoral head surface replacement system of hip joint for preservation of a blood vessel, and more particularly, to a surface replacement system for preservation of a blood vessel of a femoral head having a plurality of stems to be assembled which enables bone on-growth and prevents fracture of a femoral neck due to weakness or necrosis caused as blood vessels going to the femoral head are destroyed by a distal metal end in a conventional femoral head surface replacement system.

2. Description of the Related Art

In general, when a coxal articulation connecting a thigh region and a gluteal region requires an artificial joint replacement treatment due to osseous arthritis or femoral head necrosis, a thigh stem can be used therefore. A surface replacement system characteristically preserves blood vessels going to the bone head and stress to the calcar femorale so that one's own bone can be maintained as much as possible.

The hip joint is a classical ball-and-socket joint created by the articulation of the head of the femur with the concave socket of the acetabulum. The body weight is transferred to the lower extremity. The hip joint has a wide range of motion. If the hip joint is destroyed by osteoarthritis and avascular necrosis, it can cause severe pain and limited motion. In order to reduce hip pain and to increase functionality, total hip arthroplasty maybe necessary for some individuals who are suffering from arthritis. A conventional total hip arthroplasty is composed of a small metal ball 22-28 mm to replace the femoral head and neck; and a metal stem that attaches to the femoral shaft.

Unlike a total hip arthroplasty, a surface replacement leaves more of patient's bone in place and does not remove the femoral head and neck as in the case of total hip arthroplasty. A surface replacement system characteristically preserves the patient's own femoral head and neck so that patients can take advantage of a wide range of motion in the hip joint and reduced dislocation compared with conventional total hip arthroplasty. The concept of surface arthroplasty for the treatment of advanced arthritis of the hip in young and active patients has many attractive features because of its improved ability to preserve femoral bone compared to total hip arthroplasty.

FIG. 5 is a view illustrating a state in which a conventional femoral head surface replacement system is used. According to FIG. 5, the conventional femoral head surface replacement system includes a femoral head surface cup 1 having a cavity inside and a distal round marginal end 11 that is open in a lower end thereof, and a stem 2 fixed in inner center of the femoral head surface cup 1 and extending to a lower portion.

The actual femoral head is anatomically not a spherical shape at the peripheral margin, but is anatomically long in anterior and short in posterior. The blood supply of the femoral head is characteristic in adults. Rich subsynoival anastomoses occur at the margins of the articular cartilage. Among these vessels, the subcapsular vessels include postero-superior retinacular vessels, which provide the major blood supply to the femoral heads. These vessels enter the head through multiple small subcapsular sulcus which are located on the posterior-superior neck of the femur. Approximately, seventy percent of the blood supply of femoral heads depends on the retinacular vessels.

Conventional femoral head surface replacement is composed of a mono-block of a distal round margin and stem. Use of this conventional surface replacement system may cause damage to the main supplying blood vessel by the outer margin of the metal cup or by cementation during the operation. The main complications of conventional surface replacement systems are fractures of the femoral neck and advanced collapse of the femoral head. All of these complications are caused by not preserving the vessels of the femoral head. Also, complications are caused by using bone cement on the femoral head. Using bone cement produces fatal pulmonary embolisms intermittently. Heat generated during the hardening time of bone cement, can cause protein necrosis of the femoral head.

Insertion of the fixed length stem through the femoral head into the femoral neck in a conventional head replacement system is also difficult to operate and requires a surgeon's skill. The regular length of fixed femoral stem cannot be adjusted to each patient's state, which can vary due to personal, sexual (male or female), height and racial differences. Thus, this conventional femoral head replacing system is inconvenient to surgeons.

SUMMARY OF THE INVENTION

To solve the above and/or other problems, the present invention provides a femoral head surface replacement system which can effectively preserve blood vessels connected to the femoral head in an operation using the femoral head surface replacement system.

Also, the femoral head aspherical cup and stem can be easily separated and assembled during an operation so that a variety of stems capable of bone growth can be replaced for use according to the condition of a patient.

Also, the present invention provides a replacement system which can guarantee bone growth between the femoral stem and the bone, or stability, after the operation.

According to an aspect of the present invention, a femoral head surface replacement system includes a femoral head aspherical cup having a round cavity inside and a distal end having an open lower end, and a stem installed on the femoral head aspherical cup and extending to a lower side end thereof, wherein, in the femoral head aspherical cup, a cavity is formed so that a femoral head can be inserted therein, a conic insertion protrusion protrudes from an upper side of the cavity, and the distal end is formed of a plurality of protruding portions and groove portions and, in the stem, an insertion hole is formed corresponding to the insertion protrusion of the femoral head aspherical cup so that the stem is fixed to the femoral head aspherical cup as the insertion protrusion is forcibly inserted into the insertion hole.

BRIEF DESCRIPTION OF THE DRAWINGS

The purpose of our design is to preserve the blood vessels. The conic insertion protrusion in the center of the inner cavity of the femoral head aspherical cup is comprised of metal. A femoral head surface replacement system according to the present invention includes a femoral head aspherical cup having an inner cavity and a distal end having an open lower end and a stem installed on the femoral head aspherical cup and extending to a lower side end thereof, which looks like an umbrella skirt, to preserve blood vessels located at the junction of the femoral head and the neck.

By use of a conic insertion protrusion in the center of the inner cavity of the metal cup, a number of stems can be connected with or without cement.

Figure 1:
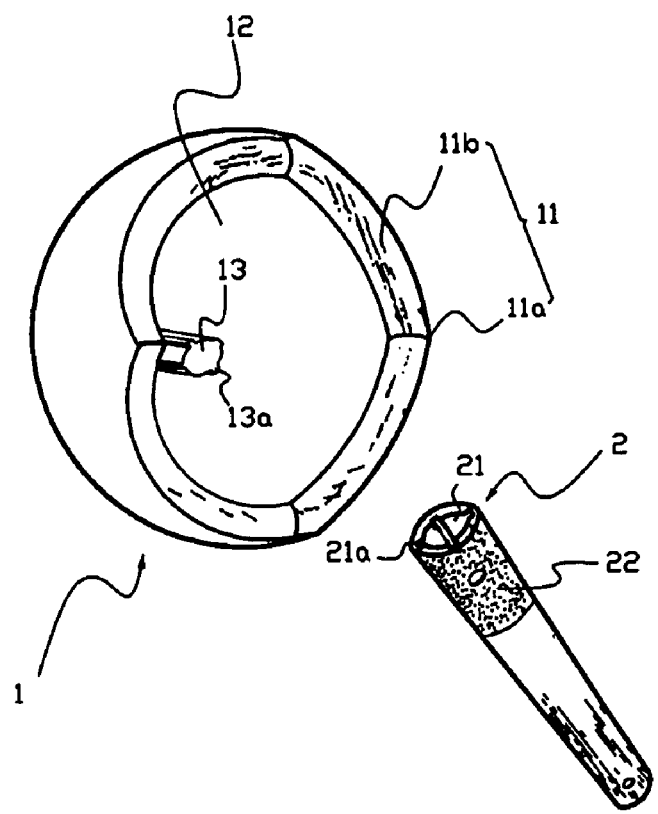
Figure 2:
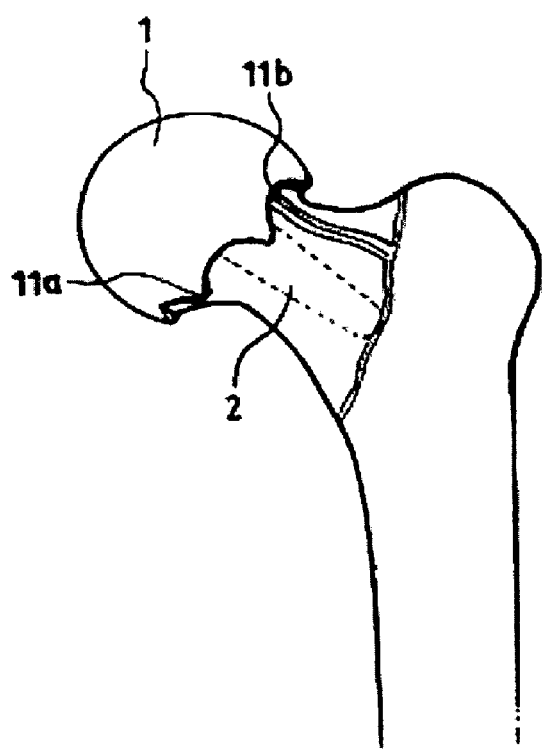
Figure 3:
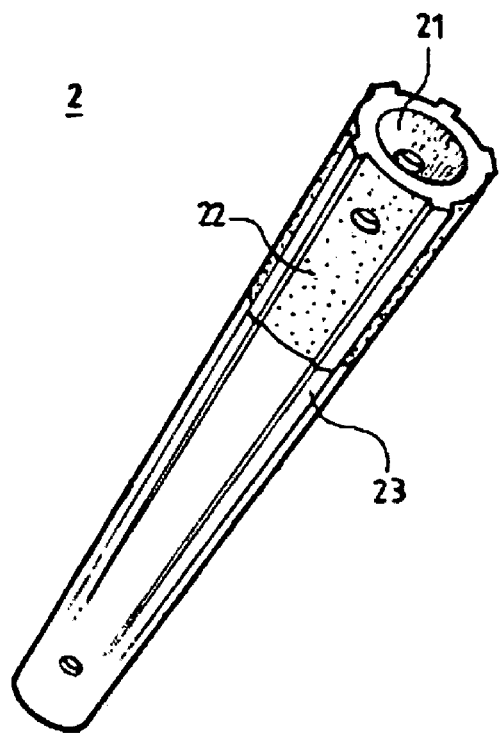
Figure 4:
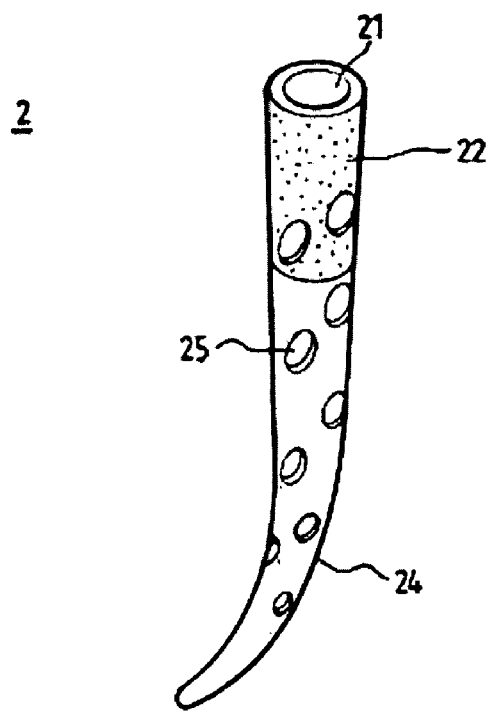
Figure 5:
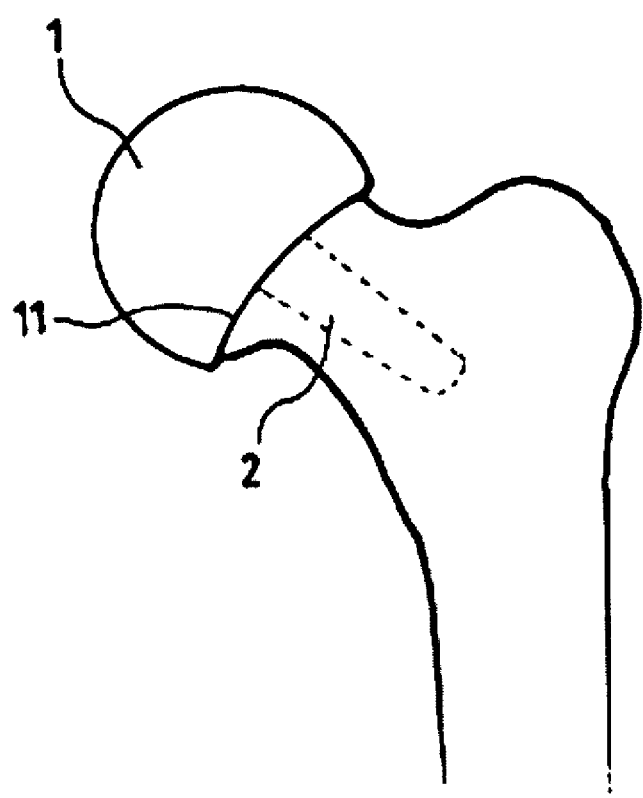

The above and other features and advantages of the present invention will become more apparent by describing in detail preferred embodiments thereof with reference to the attached drawings in which:

FIG. 1 is an exploded perspective view illustrating a femoral head surface replacement system according to an embodiment of the present invention;

FIG. 2 is a view illustrating a state in which the femoral head surface replacement system of FIG. 1 is used;

FIG. 3 is a perspective view illustrating part of a femoral head surface replacement system according to another embodiment of the present invention;

FIG. 4 is a perspective view illustrating part of a femoral head surface replacement system according to yet another embodiment of the present invention; and FIG. 5 is a view illustrating a state in which a conventional femoral head surface replacement system is used.

DETAILED DESCRIPTION OF THE INVENTION

FIG. 1 is an exploded perspective view illustrating a femoral head surface replacement system according to an embodiment of the present invention. FIG. 2 is a view illustrating a state in which the femoral head surface replacement system of FIG. 1 is used.

A femoral head surface replacement system according to an embodiment of the present invention includes a femoral head aspherical cup 1 having an inner cavity and a distal end 11 having an open lower end and a stem 2 installed on the femoral head aspherical cup 1 and extending to a lower side end thereof, which looks like an umbrella skirt.

In the femoral head aspherical cup 1, a cavity 12 is formed so that a femoral head can be inserted therein, a conic insertion protrusion 13 protrudes from an upper side of the cavity 12, and the open distal end 11 is formed of a plurality of protruding portions 11a and a plurality of groove portions 11b which form a continuous curve which looks like the edge of an umbrella. In FIGS. 1 and 2, each protruding portion is tapered to form a point at the lower end of the cup, each groove portion forms a rounded arc between two protruding points and the depth of each groove portion is shown as less than the width of each groove portion. In the embodiment shown in FIG. 1, the open distal end of the femoral head aspherical cup has four protruding portions and four groove portions. In the stem 2, an insertion hole 21 is formed corresponding to the insertion protrusion 13 of the femoral head aspherical cup 1 so that the stem 2 is fixed to the femoral head aspherical cup 1 as the insertion protrusion 13 is forcibly inserted into the insertion hole 21.

An operator prepares a femoral head aspherical cup 1 suitable for the conditions of the patient and a stem 2, which can be of various types and couples the femoral head aspherical cup 1 and the stem 2 via the conic insertion protrusion 13 and the insertion hole 21 to be installed at the operation site. At this time, the shapes and positions of the protruding portions 11a and the groove portions 11b formed on the distal end 11 of the femoral head aspherical cup 1 need to be adjusted such that the groove portion 11b is located at a position having the most blood vessels conveying blood to the femoral head and receiving the most stress.

In the present invention, a portion of the cup where major blood vessels going to the femoral head pass and the upper end portion where the most stress applies form the groove portions 11b while the other portion forms the protruding portions 11a. Thus, stress acting on the blood vessels is reduced and the stress at the portion receiving the most stress is distributed to the protruding portions 11a at either side.

Thus, the protruding portions 11a and the groove portions 11b having the same size can be formed to repeat several times. When the protruding portions 11a and the groove portions 11b are accurately manufactured considering various environments, the sizes of the protruding portions 11a and the groove portions 11b are designed to be different from each other. The description that the protruding portions 11a and the groove portions 11b are repeated does not mean that the protruding portions 11a and the groove portions 1b with the same size are not repeated.

In an embodiment of the present invention, a plurality of protrusions 13a protrude from an outer circumferential surface of the insertion portion 13 and extend in a lengthwise direction and a plurality of insertion grooves 21a corresponding thereto are formed in an inner circumferential surface of the insertion hole 21 of the stem 2.

According to this embodiment, not only is the stem 2 more easily assembled to the femoral head aspherical cup 1 but also the stem 2, which is divided into an upper part and a lower part, can be more accurately assembled. Also, according to the state of a patient, there is a need to finely adjust the angle of the stem 2 and, in such a case, the protrusions 13a and insertion grooves 21a are easily fixed in a conic shape.

In addition, a stem proximal end 22 is formed to improve coupling with respect to cement by increasing the surface roughness of part of an outer circumferential surface of the stem 2 adjacent to the insertion grooves 21. In order to fix the stem 2 to the calcar femorale more firmly, a bone cement having no side effects to the human body is hardened between the bone and the stem 2 so as to fix them together. When the surface roughness of the stem 2 increases, the adhesive force with respect to the cement increases so that the bone and the stem 2 can be more firmly coupled to each other.

FIG. 3 is a perspective view illustrating part of a femoral head surface replacement system according to another embodiment of the present invention. In the present embodiment, in addition to the increase in adhesiveness by using a stem proximal end 22 which is knife-edge-like fluted, a plurality of protruding guides 23 are formed on an outer circumferential surface of a stem 2 to extend lengthwise so that the stem can be effectively fixed with respect to a twist stress acting on the stem 2 without using the cement.

That is, although the femoral head aspherical cup 1 functioning as a femoral head is supposed to move by being engaged with a joint, since it is not avoidable that a twist stress acts on the stem 2 by loading as a man walks, fixture by cement may cause damage as the twist stress is accumulated according to the lapse of time. Thus, in the present invention, to effectively respond to the twist stress, the protruding guides 23 are formed on the outer circumferential surface of the stem. The stem 2 having the protruding guides 23 is usually used for a no cement fixture in which the twist stress and compression stress are the most.

FIG. 4 is a perspective view illustrating part of a femoral head surface replacement system according to yet another embodiment of the present invention. A stem 2 has a shape of a taper in which an outer diameter thereof decreases from an upper portion where the insertion hole 21 is formed to a lower portion where a curved portion 24 gently curved in one direction is formed close to a tip end thereof. The stem 2 having the above shape is not only used for the no cement fixture but is also advantageous by providing stability to a long bone at the initial stage.

Also, in the above embodiment, a plurality of bone growth holes 25 may be formed in the stem 2 by penetrating the same. When one's own bone piece is put inside the stem 2 during an operation, the bone piece grows together with an outside bone after the operation so that both bones are combined through the bone growth holes 25. As a result, the stem 2 and the calcar femorale are more firmly fixed.

The present embodiment can reduce a sense of heterogeneousness between the bone and the femur and a burden to the human body. Stems having a variety of shapes can be used instead of the curved stem shown in FIG. 4.

As described above, according to the present invention, the open distal end of the femoral head aspherical cup consists of the continuously arranged protruding portions and groove portions, and the stress acting on the femoral head is redirected by the femoral head aspherical cup to act toward the protruding portions. Thus, the blood vessels pass the groove portions where the action of the stress is less, so that fatigue due to the stress is distributed and the blood vessels are prevented from being damaged.

Also, since the assembly of the femoral head aspherical cup and the stem is made easy, a femoral head aspherical cup and a stem having appropriate size and shape can be chosen according to the situation of a patient so that an operation becomes simplified.

Furthermore, since the inside of the stem and the outside bone are combined after a certain amount of time after the operation, a self-bone transplant is made possible.

What is claimed is:

1. A femoral head surface replacement system including a femoral head aspherical cup having a round cavity inside and a distal end having an open lower end, and a stem installed on the femoral head aspherical cup and extending to a lower side end thereof, wherein, in the femoral head aspherical cup, a cavity is which is adapted for insertion of a patient's femoral head therein a conic insertion protrusion protrudes from an upper side of the cavity, and the distal end is formed of a plurality of protruding portions and groove portions, the lower end of the cup in each groove portion forming a rounded arc between two protruding portions at the distal end of the cup, the arc having a height and a width, the height of the arc formed by each groove portion being less than its width and, in the stem, an insertion hole is formed corresponding to the insertion protrusion of the femoral head aspherical cup so that the stem is fixed to the femoral head aspherical cup as the insertion protrusion is forcibly inserted into the insertion hole.

2. The femoral head surface replacement system of claim 1, wherein a plurality of protrusions protrude from an outer circumferential surface of the insertion protrusion and extend in a lengthwise direction and a plurality of insertion grooves are formed corresponding to the protrusions in an inner circumferential surface of the insertion hole of the stem.

3. The femoral head surface replacement system of claim 2, wherein a stem proximal end is formed to improve coupling with respect to cement by increasing the surface roughness of part of an outer circumferential surface of the stem adjacent to the insertion grooves.

4. The femoral head surface replacement system of claim 1, wherein a plurality of protruding guides are formed on the outer circumferential surface of the stem which extends lengthwise.

5. The femoral head surface replacement system of claim 1, wherein the stem has a shape of a taper in which the outer diameter thereof decreases from the upper portion where the insertion hole is formed to a lower portion where a curved portion gently curved in one direction is formed close to the tip end thereof.

6. The femoral head surface replacement system of claim 1, wherein a plurality of bone growth holes is formed in the stem by penetrating the stem.

7. The femoral head surface replacement system of claim 1, wherein each protruding portion is tapered to form a point at the distal end of the cup.

* * * * *